United States Patent
Gutkowicz-Krusin et al.

(10) Patent No.: US 6,307,957 B1
(45) Date of Patent: *Oct. 23, 2001

(54) MULTISPECTRAL IMAGING AND CHARACTERIZATION OF BIOLOGICAL TISSUE

(75) Inventors: Dina Gutkowicz-Krusin, Princeton, NJ (US); Marek Elbaum, Dobbs Ferry; Michael Greenebaum, Brooklyn, both of NY (US); Adam Jacobs, Woodcliff Lake, NJ (US); Alexandru Bogdan, New York, NY (US)

(73) Assignee: Electro-Optical Sciences Inc, Irvington-on-Hudson, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/604,645

(22) Filed: Jun. 27, 2000

Related U.S. Application Data

(63) Continuation-in-part of application No. 09/031,929, filed on Feb. 27, 1998, now Pat. No. 6,081,612, and a continuation-in-part of application No. 09/032,450, filed on Feb. 27, 1998, now Pat. No. 6,028,749.
(60) Provisional application No. 60/039,218, filed on Feb. 28, 1997, and provisional application No. 60/039,407, filed on Feb. 28, 1997.

(51) Int. Cl.[7] ............................. G06K 9/00; G06K 9/34; G06K 9/48; A61B 1/04; H04B 1/66
(52) U.S. Cl. ..................... 382/128; 382/173; 382/191; 348/45
(58) Field of Search ................................... 382/128, 133, 382/173, 190, 191, 199, 203; 362/574; 348/45; 375/240.19

(56) References Cited

U.S. PATENT DOCUMENTS 6,081,612 * 6/2000 Gutkowicz-Krusin et al. ..... 382/128

OTHER PUBLICATIONS

Zhong et al, "Compact Image Representation from Multi-scale Edges"; IEEE Paper ISBN: 0-8186-2057-9, pp. 522-525, Dec. 1990.*

* cited by examiner

*Primary Examiner*—Amelia M. Au
*Assistant Examiner*—Mehrdad Dastouri
(74) *Attorney, Agent, or Firm*—Rodney T. Hodgson

(57) ABSTRACT

A light image is conveyed from a biological tissue through a flexible optical system to an image receiver, where it is converted to a form which may be entered into a computer. The computer segments the image by generating a segmentation mask defining the boundary of a region of interest in at least one spectral band, estimates at least one rotationally and translationally invariant statistical measure of coefficient distributions of the multiscale wavelet maxima representations of the digital images in at least one spectral band, characterizes the condition of the tissue based on the estimated values, and outputs the characterization of the condition of the tissue.

15 Claims, 1 Drawing Sheet

MULTISPECTRAL IMAGING AND CHARACTERIZATION OF BIOLOGICAL TISSUE

CROSS REFERENCE TO RELATED APPLICATIONS

This application is a continuation-in-part (CIP) of U.S. application Ser. No. 09/031,929 filed Feb. 27, 1998, (now U.S. Pat. No. 6,081,612) and U.S. application Ser. No. 09/032,450 filed Feb. 27, 1998, now U.S. Pat. No. 6,208,749 B1 issued on Mar. 27, 2001, which claim priority pursuant to 35 U.S.C. 119(e) to the U.S. Provisional Applications: Application No. 60/039,218 and Application No. 60/039,407, both filed Feb. 28, 1997.

FIELD OF THE INVENTION

The field of the invention is the field of automatic machine vision and classification, in particular to the field of classification of biological tissue from images of the biological tissue.

BACKGROUND OF THE INVENTION

The background of the invention is covered in great detail in the above identified copending applications, which are included by reference. Not included in the above references are references to conducting light from place to place so that the image is conserved.

OBJECTS OF THE INVENTION

It is an object of the invention to illuminate and image biological tissue, principally in vivo, and to convey the image in the form of light to an image receiver for conversion to electrical signals and for automatic recognition of biological features.

SUMMARY OF THE INVENTION

A light image is conveyed from a biological tissue through a flexible optical system to an image receiver, where it is converted to a form which may be entered into a computer. The computer segments the image by generating a segmentation mask defining the boundary of a region of interest in at least one spectral band, estimates at least one rotationally and translationally invariant statistical measure of coefficient distributions of the multiscale wavelet maxima representations of the digital images in at least one spectral band, characterizes the condition of the tissue based on the estimated values, and outputs the characterization of the condition of the tissue.

DETAILED DESCRIPTION OF THE INVENTION

Figure 1:
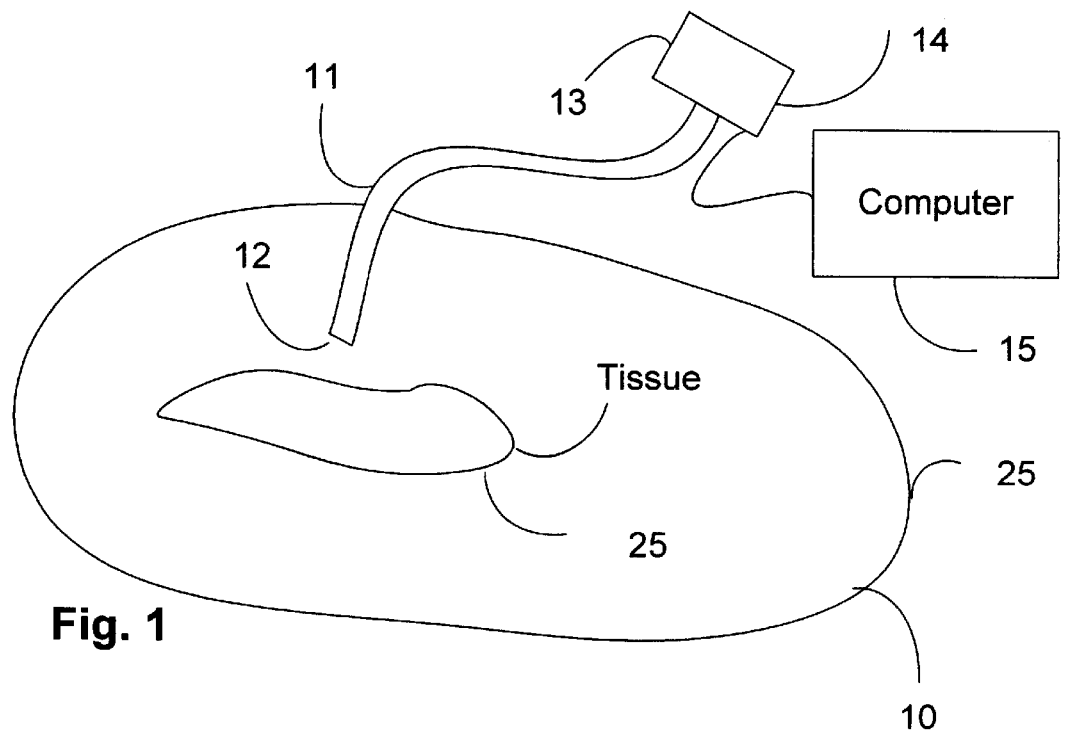
FIG. 1 is a sketch of the system of the invention.

FIG. 1 shows a sketch of the system of the invention. A patient 10 has a flexible endoscope 11 inserted into a natural or surgically provided orifice of the body. As is very well known in the art of endoscopy, light is provided for illuminating the tissue inside the body, and the light reflected from the tissue and scattered from under the surface of the tissue falls on the end 12 of the endoscope. The first end of the endoscope 12 generally has a lens (not shown) which images the tissue on to the end of a coherent fiber bundle (not shown). The light imaged on to the fiber bundle is carried to the other end of the endoscope 13, where it may be projected on to a film or an electronic image receiver 14 such as are found in video or digital cameras. The output of the image receiver is carried to a processor or computer 15 where the computer segments the image by generating a segmentation mask defining the boundary of a region of interest in at least one spectral band, estimates at least one rotationally and translationally invariant statistical measure of coefficient distributions of the multiscale wavelet maxima representations of the digital images in at least one spectral band, characterizes the condition of the tissue based on the estimated values, and outputs the characterization of the condition of the tissue. The computer processes are described in great detail in the above identified applications.

Figure 2:
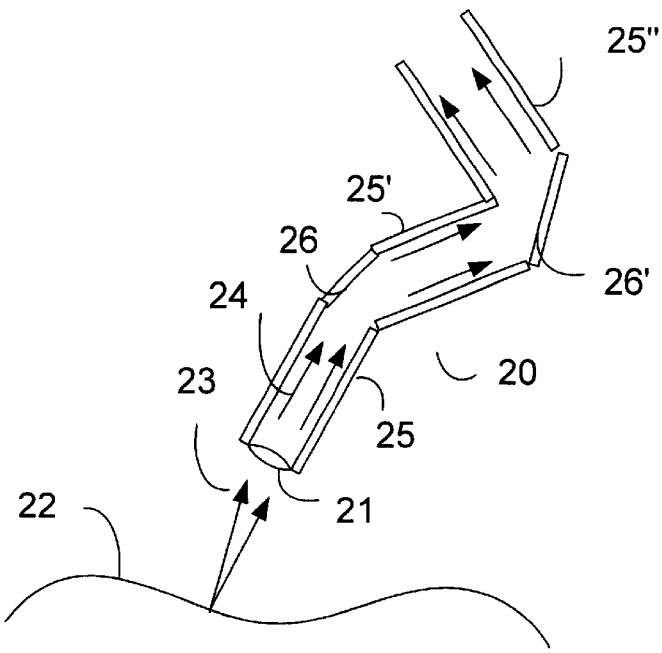
FIG. 2 is a sketch of an articulated arm of a system of the invention.

FIG. 2 shows a sketch of an articulated arm 20 for conveying the images. The articulated arm is especially useful when the illuminating light is of a wavelength which is not transmitted well by the glass used in typical endoscopes. A lens 21 is placed so that the tissue to be imaged 22 is removed from the lens 21 by the focal distance l of the lens 22. Light 23 diverging from the tissue 22 is converted to a parallel beam 24 which propagates through a tube 25. The parallel light beam 24 may be reflected from mirrors 26 and 26' mechanically set to direct the beam 24 through other tubes 25' and 25" flexibly connected to tube 25. Tubes 25, 25', and 25" may rotate on their axis to change the plane of propagation of the light beam 24. When the light beam 24 exits the articulated arm, it may be focused on an image receiver (not shown) to capture an image of the tissue 22.

Obviously, many modifications and variations of the present invention are possible in light of the above teachings. It is therefore to be understood that, within the scope of the appended claims, the invention may be practiced otherwise than as specifically described.

We claim:

1. A method of characterizing the condition of a region of interest of biological tissue, wherein the absorption and scattering of light in different spectral bands by the region of interest is a function of the condition of the tissue, the method comprising:

illuminating a portion of the tissue including the region of interest by light in at least one spectral band;

conveying an image of the region of interest through an optical system to an image receiver;

imaging a portion of the tissue including the region of interest at the at least one spectral band with the light re-emitted by the portion of the tissue to generate at least one digital image comprising signals whose values are a function of the condition of the region of interest of the tissue; and providing the digital images to a processor, wherein the processor:

segments the digital images by generating a segmentation mask defining the boundary of the region of interest from a digital image in any one of the at least one spectral bands;

estimates at least one rotationally and translationally invariant statistical measure of coefficient distributions of the multiscale wavelet maxima representations of the digital image;

characterizes the condition of the tissue based on the estimated values; and outputs the characterization of the condition of the tissue.

2. The method of claim 1, wherein the at least one statistical measure is calculated separately within either of a border region and an interior region of the digital image, wherein:

the border region encompasses the envelope of circles of fixed radius centered on the boundary of the segmentation mask; and the inside region comprises all points of the image that are within the segmentation mask boundary but not included in the border region.

3. The method of claim 2, wherein the computing step comprises estimating at an individual level at least one value which is a statistical measure of texture of the portion of the region of interest within the border region and interior region, chosen from the group consisting of:

the number of wavelet maxima per unit area;

the ratio of the mean coefficient magnitude to the absolute deviation of the coefficient magnitudes from the mean value;

the ratio of the mean coefficient magnitude to the standard deviation of the coefficient magnitude; and the skewness of the coefficient magnitude, normalized to the cube of the standard deviation.

4. The method of claim 1, further comprising estimating either of the degree of change of a statistic of the wavelet coefficient distribution with increment of wavelet level, and the degree of deviation of such change from linearity.

5. The method of claim 2, further comprising estimating the average rate of change, with respect to level, of the number of wavelet maxima per unit area.

6. The method of claim 1, further comprising comparing the estimated texture values to the threshold derived from statistical analysis of a multiscale wavelet transformation of the digital image.

7. The method of claim 1, wherein the estimating and characterizing steps are conducted without the intervention of an operator.

8. The method of claim 1, wherein the segmenting step is conducted without the intervention of an operator.

9. The method of claim 1, where the optical system is an endoscope.

10. The method of claim 1, where the optical system is a fiber optic bundle.

11. The method of claim 1, where the optical system is an articulated arm.

12. A system for characterizing the condition of a region of interest of tissue, comprising:

a source of light for illuminating the region of interest in at least one spectral band;

an optical system for conveying the image of the region of interest to an image receiver;

an image receiver for acquiring digital images of the region of interest based on the light re-emitted from the illuminated region of interest at each of the spectral bands, the digital image comprising digital signals whose values are a function of the condition of the region of interest;

memory for storing the digital images provided by the image receiver;

a digital processor programmed to perform the steps of:
segmenting the digital images stored in memory by generating a segmentation mask from a digital image in any one of the at least one spectral band;

estimating at least one rotationally and translationally invariant statistical measure of coefficient distributions for the multiscale wavelet maxima representations of the digital images in each spectral band, which are functions of the texture of the region of interest determined by the segmentation mask;

characterizing the condition of the tissue based on the estimated values; and outputting the characterization of the region of interest.

13. The system of claim 12, where the flexible optical system is an endoscope.

14. The system of claim 12, where the flexible optical system is a fiber optic bundle.

15. The system of claim 12, where the flexible optical system is an articulated arm.

* * * * *